United States Patent [19]

Maurer et al.

[11] 4,380,538
[45] Apr. 19, 1983

[54] COMBATING ARTHROPODS WITH O-ALKYL-O-(2-CYCLOPROPYL-6-SUB-STITUTED-METHYL-PYRIMIDIN-4-YL)-(THIONO)(THIOL) PHOSPHORIC (PHOSPHONIC) ACID ESTERS AND ESTER-AMIDES

[75] Inventors: Fritz Maurer; Rolf Schröder, both of Wuppertal; Ingeborg Hammann, Cologne; Wilhelm Stendel, Wuppertal, all of Fed. Rep. of Germany

[73] Assignee: Bayer Aktiengesellschaft, Leverkusen, Fed. Rep. of Germany

[21] Appl. No.: 48,857

[22] Filed: Jun. 15, 1979

[30] Foreign Application Priority Data

Jul. 13, 1978 [DE] Fed. Rep. of Germany ....... 2830766

[51] Int. Cl.³ ..................... A01N 57/16; A01N 57/24; A01N 57/32; C07F 9/65
[52] U.S. Cl. .................................. 424/200; 544/243; 544/319
[58] Field of Search ......................... 544/243; 424/200

[56] References Cited

U.S. PATENT DOCUMENTS 4,012,506 3/1977 Balke et al. .................. 424/200
4,168,304 9/1979 Mauer et al. .................. 424/200

FOREIGN PATENT DOCUMENTS 887 3/1979 European Pat. Off. .
1063067 4/1954 France .
2378791 1/1977 France .

Primary Examiner—Donald G. Daus
Assistant Examiner—Diana G. Rivers
Attorney, Agent, or Firm—Sprung, Horn, Kramer & Woods

[57] ABSTRACT

O-alkyl-O-(2-cyclopropyl-6-substituted-methyl-pyrimidin-4-yl)-(thiono)(thiol) phosphoric (phosphonic) acid esters and ester-amides of the formula

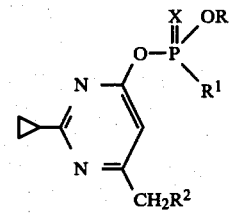

in which
R is alkyl,
R¹ is alkyl, alkoxy, alkylthio, alkylamino or phenyl,
R² is alkoxy or alkylthio, and
X is oxygen or sulphur,
which possess arthropodicidal properties.

9 Claims, No Drawings

COMBATING ARTHROPODS WITH O-ALKYL-O-(2-CYCLOPROPYL-6-SUBSTITUTED-METHYL-PYRIMIDIN-4-YL)-(THIONO)(THIOL) PHOSPHORIC (PHOSPHONIC) ACID ESTERS AND ESTER-AMIDES

The present invention relates to and has for its objects the provision of particular new O-alkyl-O-(2-cyclopropyl-6-substituted-methyl-pyrimidin-4-yl)-(thiono)(thiol) phosphoric (phosphonic) acid esters and ester-amides which possess arthropodicidal properties, active compositions in the form of mixtures of such compounds with solid and liquid dispersible carrier vehicles, and methods for producing such compounds and for using such compounds in a new way especially for combating pests, e.g. insects and acarids, with other and further objects becoming apparent from a study of the within specification and accompanying examples.

It is known that certain pyrimidinyl-thionophosphoric acid esters, for example O,O-diethyl-O-(2-methylthio-6-methyl-pyrimidin-4-yl)-thionophosphoric acid ester, have insecticidal and acaricidal properties (see German Patent Specification No. 910,652).

However, the action of these compounds is not always satisfactory, especially when low amounts and concentrations are used.

The present invention now provides, as new compounds, the 2-cyclopropyl-pyrimidin-4-yl-(thiono)(thiol)-phosphoric(phosphonic) acid esters and ester-amides of the general formula

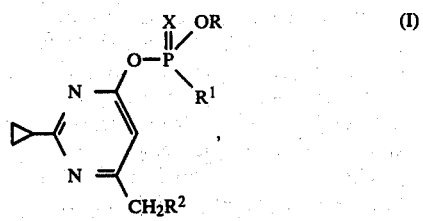

in which
R represents alkyl,
R¹ represents alkyl, alkoxy, alkylthio, alkylamino or phenyl,
R² represents alkoxy or alkylthio and
X represents oxygen or sulphur.

Preferably, in formula (I), R represents straight-chain or branched alkyl with 1 to 5 (especially with 1 to 3) carbon atoms, R¹ represents straight-chain or branched alkyl with 1 to 5 (especially with 1 to 3) carbon atoms, straight-chain or branched alkoxy, alkylthio or alkylamino with 1 to 5 (especially with 1 to 3) carbon atoms per alkyl radical, or phenyl, and R² represents straight-chain or branched alkoxy or alkylthio with 1 to 5 (especially with 1 to 3) carbon atoms per alkyl radical.

Surprisingly, the 2-cyclopropyl-pyrimidin-4-yl-(thiono)(thiol)-phosphoric(phosphonic) acid esters and ester-amides according to the invention exhibit a better activity in combating pests, in particular a better insecticidal and acaricidal action, than the corresponding compounds of analogous structure and the same type of action which are known from the state of the art. The products according to the present invention thus represent a valuable enrichment of the art.

The invention also provides a process for the preparation of a 2-cyclopropyl-pyrimidin-4-yl-(thiono)(thiol)-phosphoric(phosphonic) acid ester or ester-amide of the formula (I) in which a (thiono)(thiol)phosphoric(phosphonic) acid ester halide or (thiono)-phosphoric acid ester-amide halide of the general formula

in which
R, R¹ and X have the meanings stated above and
Hal represents chlorine or bromine,
is reacted with a 2-cyclopropyl-4-hydroxy-pyrimidine of the general formula

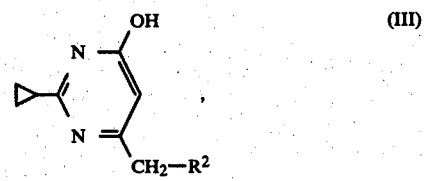

in which
R² has the meaning stated above, if appropriate in the presence of an acid acceptor and if appropriate in the presence of a diluent.

If, for example, O-n-propyl-n-propane-phosphonic acid ester chloride and 2-cyclopropyl-6-ethoxymethyl-4-hydroxy-pyrimidine are used as starting compounds, the reaction which proceeds can be outlined by the equation which follows:

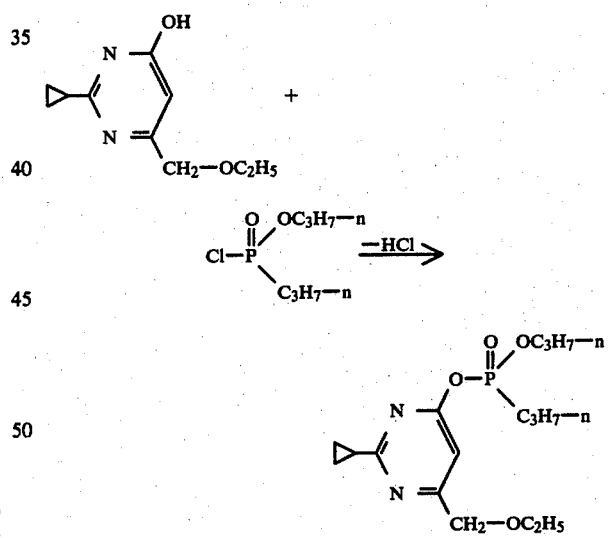

The formula (II) provides a definition of the (thiono)(thiol)-phosphoric(phosphonic) acid ester halides and (thiono)-phosphoric acid ester-amide halides to be used as starting substances. Preferably, in this formula, R and R¹ have the meanings stated as preferred in connection with formula (I), while Hal preferably represents chlorine.

The starting substances of the formula (II) are known compounds. Examples of these compounds which may be mentioned are: O-methyl-, O-ethyl-, O-n-propyl- and O-iso-propyl-methane-, -ethane-, -propane- and -phenyl-phosphonic acid ester chloride and the corresponding thiono analogues; O,O-dimethyl-, O,O-diethyl-, O,O-di-n-propyl-, O-methyl-O-ethyl-, O-methyl-O-n-propyl-, O-methyl-O-iso-propyl-, O-ethyl-O-n-propyl- and O-ethyl-O-iso-propyl-phosphoric acid diester chloride and the corresponding thiono analogues; O,S-dimethyl-, O,S,-diethyl-, O,S-di-n-propyl-, O,S-di-iso-propyl-, O-methyl-S-ethyl-, O-methyl-S-n-propyl-, O-methyl-S-iso-propyl-, O-ethyl-S-methyl-, O-ethyl-S-n-propyl-, O-ethyl-S-iso-propyl-, O-n-propyl-S-methyl-, O-n-propyl-S-ethyl-, O-n-propyl-S-iso-propyl-, O-iso-propyl-S-methyl-, O-iso-propyl-S-ethyl- and O-iso-propyl-S-n-propyl-thiolphosphoric acid diester chloride and the corresponding thiono analogues; and O-methyl-N-methyl-, O-methyl-N-ethyl-, O-methyl-N-n-propyl-, O-methyl-N-iso-propyl-, O-ethyl-N-methyl-, O-ethyl-N-ethyl-, O-ethyl-N-n-propyl-, O-ethyl-N-iso-propyl-, O-propyl-N-methyl-, O-n-propyl-N-ethyl-, O-n-propyl-N-n-propyl-, O-n-propyl-N-iso-propyl-, O-iso-propyl-N-methyl-, O-iso-propyl-N-ethyl, O-iso-propyl-N-n-propyl- and O-iso-propyl-N-iso-propyl-phosphoric acid ester-amide chloride and the corresponding thiono analogues.

Formula (III) provides a definition of the 2-cyclopropyl-4-hydroxy-pyrimidines also to be used as starting substances. Preferably, in this formula, $R^2$ has the meaning stated as preferred in connection with formula (I).

The 2-cyclopropyl-4-hydroxy-pyrimidines of the formula (III) have not hitherto been described in the literature. These compounds are obtained by reacting the corresponding γ-alkoxy- or γ-alkylthio-acetoacetic acid methyl ester or ethyl ester with cyclopropanecarboxylic acid amidine hydrochlorides at temperatures between −10° and +100° C., preferably between 0° and 50° C., if appropriate in the presence of an acid acceptor, for example sodium methylate, and if appropriate in the presence of a diluent, for example methanol. For working up, the solvent is stripped off in vacuo, the residue is dissolved in ice-water, the solution is adjusted to pH 5 with hydrochloric acid and the product which separates out is isolated by vacuum filtration.

Specific examples which may be mentioned of the compounds of the formula (III) are: 6-methoxymethyl-, 6-ethoxymethyl-, 6-n-propoxymethyl- and 6-iso-propoxymethyl-2-cyclopropyl-4-hydroxy-pyrimidine and 6-methylthiomethyl-, 6-ethylthiomethyl-, 6-n-propylthiomethyl- and 6-iso-propylthiomethyl-2-cyclopropyl-4-hydroxy-pyrimidine.

The process for the preparation of the 2-cyclopropyl-pyrimidin-4-yl-(thiono)(thiol)-phosphoric(phosphonic) acid esters and ester-amides according to the invention is preferably carried out using a suitable solvent or diluent. Possible solvents and diluents are virtually any of the inert organic solvents, especially aliphatic and aromatic, optionally chlorinated hydrocarbons, such as benzine, benzene, toluene, xylene, methylene chloride, chloroform, carbon tetrachloride, chlorobenzene and o-dichlorobenzene; ethers, such as diethyl ether, dibutyl ether, tetrahydrofuran and dioxane; ketones, such as acetone, methyl ethyl ketone, methyl isopropyl ketone and methyl isobutyl ketone; and nitriles, such as acetonitrile and propionitrile.

Any of the customary acid-binding agents can be used as the acid acceptor. Alkali metal carbonates and alcoholates, such as sodium carbonate and potassium carbonate, and sodium methylate or ethylate and potassium methylate or ethylate, and aliphatic, aromatic or heterocyclic amines, for example triethylamine, trimethylamine, dimethyl-aniline, dimethylbenzylamine and pyridine, have proved particularly suitable.

The reaction temperature can be varied within a substantial range. In general, the reaction is carried out at from −10° to +100° C., preferably at from 10° to 80° C. The process according to the invention is generally carried out under normal pressure.

For carrying out the process according to the invention, 1.0 to 1.2 moles of 2-cyclopropyl-4-hydroxypyrimidine (III) are preferably employed per mole of (thiono)(thiol)-phosphoric(phosphonic) acid ester halide or (thiono)-phosphoric acid ester-amide halide (II). In general, the reaction is carried out in one of the diluents indicated, in the presence of an acid acceptor, and the reaction mixture is stirred at the required temperature for several hours. Thereafter, an organic solvent, for example toluene, is added to the mixture and the organic phase is worked up in the customary manner, by washing and drying and distilling off the solvent.

The new compounds are obtained in the form of oils, some of which cannot be distilled without decomposition, but which may be freed from the last volatile constituents by so-called "incipient distillation", that is to say by prolonged heating to moderately elevated temperatures under reduced pressure, and may be purified in this manner. The refractive index is used for their characterization.

The 2-cyclopropyl-pyrimidin-4-yl-(thiono)(thiol)-phosphoric(phosphonic) acid esters and ester-amides according to the invention are distinguished, in particular, by an outstanding insecticidal and acaricidal activity against plant pests, pests harmful to health, pests of stored products and ectoparasites. They have a very good action against sucking and biting insects and mites.

For this reason, the compounds according to the invention can successfully be employed as agents for combating pests in plant protection and in the hygiene field and in the field of protection of stored products and of veterinary medicine.

The active compounds are well tolerated by plants, have a favourable level of toxicity to warm-blooded animals, and can be used for combating arthropod pests, especially insects and acarids, which are encountered in agriculture, in forestry, in the protection of stored products and of materials, and in the hygiene field. They are active against normally sensitive and resistant species and against all or some stages of development. The abovementioned pests include:

from the class of the Isopoda, for example *Oniscus asellus, Armadillidium vulgare* and *Porcellio scaber;* from the class of the Diplopoda, for example *Blaniulus guttulatus;* from the class of the Chilopoda, for example *Geophilus carpophagus* and Scutigera spec.;

from the class of the Symphyla, for example *Scutigerella immaculata;* from the order of the Thysanura, for example *Lepisma saccharina;* from the order of the Collembola, for example *Onychiurus armaturs;* from the order of the Orthoptera, for example *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria;* from the order of the Dermaptera, for example *Forficula auricularia;* from the order of the Isoptera, for example Reticulitermes spp.;

from the order of the Anoplura, for example *Phylloxera vastatrix,* Pemphigus spp., *Pediculus humanus corporis,* Haematopinus spp. and Linognathus spp.;

from the order of the Mallophaga, for example Trichodectes spp. and Damalinea spp.;

from the order of the Thysanoptera, for example *Hercinothrips femoralis* and *Thrips tabaci;* from the order of the Heteroptera, for example Eurygaster spp., *Dysdercus intermedius, Piesma quadrata, Cimex lectularius, Rhodnius prolixus* and Triatoma spp.;

from the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.;

from the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Cacoecia podana, Capua reticulana, Choristoneura fumiferana, Clysia ambiguella, Homona magnanima* and *Tortrix viridana;* from the order of the Coleoptera, for example *Anobium punctatum, Rhizopertha dominica, Bruchidius obtectus, Acanthoscelides obtectus, Hylotrupes, bajulus, Agelastica alni, Leptinotarsa decemlineate, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica;* from the order of the Hymenoptera, for example Diprion spp., Hoplocampa spp., Lasius spp., *Monomorium pharaonis* and Vespa spp.;

from the order of the Diptera, for example Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa;* from the order of the Siphonaptera, for example *Xenopsylla cheopis* and Ceratophyllus spp.;

from the class of the Arachnida, for example *Scorpio maurus* and *Latrodectus mactans;* from the order of the Acarina, for example *Acarus siro,* Argas spp., Ornithodoros spp., *Dermanyssus gallinae, Eriophyes ribis, Phyllocoptruta oleivora, Boophilus* spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp.

The active compounds can be converted into the customary formulations, such as solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice,, sepiolite and dolomite, as well as synthetic granules of inorganic and organic meals, and granules of organic material such as sawdust, coconut shells, corn cobs andd tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention may be used in the form of their formulations of the types that are commercially available or in the use forms prepared from these formulations.

The active compound content of the use forms prepared from the formulations of the types that are commercially available can vary within wide ranges. The active compound concentration of the use forms can be from 0.0000001 to 100% by weight of active compound, preferably from 0.01 to 10% by weight.

The compounds may be employed in a customary manner appropriate for the particular use forms.

When used against pests harmful to health and pests of stored products, the active compounds are distinguished by an excellent residual activity on wood and clay as well as a good stability to alkali on limed substrates.

In the veterinary field, the active compounds according to the invention may be used in a known manner, such as orally in the form of, for example, tablets, capsules, drenches and granules; dermally by means of, for example, dipping, spraying, pouring-on, spotting-on and powdering; and parenterally, for example by means of injections.

The present invention also provides an arthropodicidal composition containing as active ingredient a compound of the present invention in admixture with a solid or liquefied gaseous diluent or carrier or in admixture with a liquid diluent or carrier containing a surface-active agent.

The present invention also provides a method of combating arthropods (especially insects and acarids) which comprises applying to the arthropods, or to a habitat thereof, a compound of the present invention alone or in the form of a composition containing as active ingredient a compound of the present invention in admixture with a diluent or carrier.

The present invention also provides a method of freeing or protecting domesticated animals from parasitical insects or acarids which comprises applying to said animals a compound according to the present invention, in admixture with a diluent or carrier.

The present invention further provides crops protected from damage by arthropods by being grown in areas in which immediately prior to and/or during the time of the growing a compound of the present invention was applied alone or in admixture with a diluent or carrier.

It will be seen that the usual methods of providing a harvested crop may be improved by the present invention.

The present invention further provides domesticated animals whenever freed or protected from parasitical insects or acarids by the application to said animals of a compound according to the present invention, in admixture with a diluent or carrier.

The preparation of the novel compounds is shown in the following illustrative example:

EXAMPLE 1

(a) The 2-cyclopropyl-4-hydroxy-pyrimidines required as starting substances can be prepared, for example, as follows:

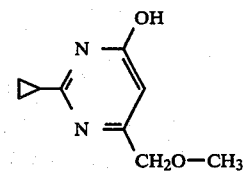

63 g (0.3 mol) of sodium methylate in methanol were added to a solution of 20 g (0.16 mol) of cyclopropanecarboxylic acid amidine hydrochloride and 21.9 g (0.15 mol) of γ-methoxyacetoacetic acid methyl ester in 150 ml of methanol at 5° C. The mixture was stirred at room temperature for 3 hours and the solvent was then stripped off under reduced pressure. The residue was dissolved in 200 ml of ice-water, the solution was brought to a pH of about 5 with concentrated hydrochloric acid, while cooling externally, and the precipitate was filtered off and dried over phosphorus pentoxide in a desiccator. 18 g (67% of theory) of 2-cyclopropyl-6-methoxy-methyl-4-hydroxy-pyrimidine were obtained in the form of a white powder with a melting point of 178° C.

2-Cyclopropyl-6-methylmercaptomethyl-4-hydroxypyrimidine with the melting point of 150° C. was prepared analogously in 60% yield.

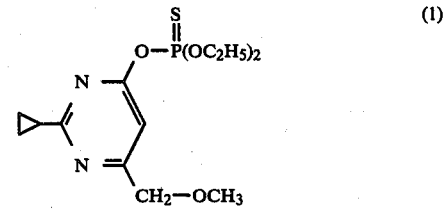

A mixture of 150 ml of acetonitrile, 9.9 g (55 mol) of 2-cyclopropyl-6-methoxymethyl-4-hydroxy-pyrimidine and 8.4 g (60 mmol) of potassium carbonate was stirred at 50° C. for one hour. The mixture was then cooled to room temperature and 9.4 g (50 mmol) of O,O-diethylthionophosphoric acid diester chloride were added. After stirring the mixture at 50°–60° C. for four hours, the reaction solution was shaken with 200 ml of water and 300 ml of toluene, the phases were separated and the organic phase was dried over magnesium sulphate and, after filtration, the toluene was stripped off from the filtrate under reduced pressure in a rotary evaporator. 14 g (85% of theory) of O,O-diethyl-O-(2-cyclopropyl-6-methoxymethyl-pyrimidin-4-yl)-thionophosphoric acid ester remained in the form of a yellow oil having a refractive index $n_D^{20}$ of 1.5483.

The following compounds of the formula

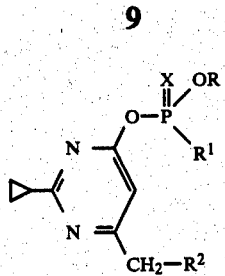

could be prepared analogously:

TABLE 1

| Compound No. | R | R¹ | R² | X | Yield (% of theory) | Refractive index: |
|---|---|---|---|---|---|---|
| 2 | $C_2H_5$ | $C_2H_5$ | $OCH_3$ | S | 81 | $n_D^{20}$: 1.5239 |
| 3 | $C_2H_5$ | ⌬ | $OCH_3$ | S | 91 | $n_D^{20}$: 1.5673 |
| 4 | $CH_3$ | $OCH_3$ | $OCH_3$ | S | 81 | $n_D^{20}$: 1.5302 |
| 5 | $C_2H_5$ | $OC_2H_5$ | $OCH_3$ | O | | |
| 6 | $C_2H_5$ | $SC_3H_7-n$ | $OCH_3$ | S | 90 | $n_D^{20}$: 1.5360 |
| 7 | $C_2H_5$ | $NH-C_3H_7-iso$ | $OCH_3$ | S | | |
| 8 | $C_2H_5$ | $OC_2H_5$ | $SCH_3$ | S | 75 | $n_D^{24}$: 1.5401 |
| 9 | $C_2H_5$ | $C_2H_5$ | $SCH_3$ | S | 74 | $n_D^{24}$: 1.5608 |
| 10 | $C_2H_5$ | ⌬ | $SCH_3$ | S | | |
| 11 | $C_2H_5$ | $OC_2H_5$ | $SC_2H_5$ | S | | |
| 12 | $C_2H_5$ | $OC_2H_5$ | $SC_3H_7-n$ | S | | |
| 13 | $C_3H_7-iso$ | $CH_3$ | $OCH_3$ | S | 91 | $n_D^{20}$: 1.5258 |
| 14 | $C_2H_5$ | $CH_3$ | $OCH_3$ | S | 81 | $n_D^{20}$: 1.5371 |
| 15 | $C_2H_5$ | $SC_3H_7-n$ | $SCH_3$ | O | | |

The insecticidal or acaricidal activity of the compounds of this invention is illustrated by the following examples wherein the compounds according to the present invention are each identified by the number (given in brackets) from Example 1:

EXAMPLE 2

Plutella test

Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage leaves (Brassica oleracea) were treated by being dipped into the preparation of active compound of the desired concentration and were infested with caterpillars of the diamond-back moth (Plutella maculipennis), as long as the leaves were still moist.

After the specified periods of time, the degree of destruction was determined as a percentage: 100% meant that all of the caterpillars were killed whereas 0% meant that none of the caterpillars were killed.

In this test, for example, the following compounds showed a superior activity compared to the prior art: (1), (2), (3), (4), (6), (8), (9), (13) and (14).

EXAMPLE 3

Tetranychus test (resistant)

Solvent: 3 parts by weight of acetone
Emulsifier: 1 part by weight of alkylaryl polyglycol ether To produce a suitable preparation of active compound, 1 part by weight of the active compound was mixed with the stated amount of solvent and the stated amount of emulsifier and the concentrate was diluted with water to the desired concentration.

Bean plants (Phaseolus vulgaris) which were heavily infested with the two-spotted spider mite (Tetranychus urticae) in all stages of development were treated by being dipped into the preparation of the active compound of the desired concentration.

After the specified periods of time, the degree of destruction was determined as a percentage: 100% meant that all of the spider mites were killed whereas 0% meant that none of the spider mites were killed.

In this test, for example, the following compounds showed a superior activity compared to the prior art: (1), (2), (8), (9), (13) and (14).

EXAMPLE 4

Test with parasitic adult cattle ticks (Boophilus microplus res.)

Solvent: Alkylaryl polyglycol ether

To produce a suitable preparation of active compound, the active substance in question was mixed with the stated solvent in the ratio of 1:2 and the concentrate thus obtained was diluted with water to the desired concentration.

10 adult cattle ticks (B. microplus res.) were dipped for 1 minute into the active compound preparation to be tested. After transfer into plastic beakers and storage in a climatically controlled chamber, the degree of destruction was determined.

In this test, for example, the following compounds showed a superior action compared to the prior art: (3), (4), (6) and (14).

It will be appreciated that the instant specification and examples are set forth by way of illustration and not limitation, and that various modifications and changes may be made without departing from the spirit and scope of the present invention.

What is claimed is:

1. An O-alkyl-O-(2-cyclopropyl-6-substituted-methyl-pyrimidin-4-yl)-(thiono) (thiol)-phosphoric (phosphonic) acid ester or ester-amide of the formula

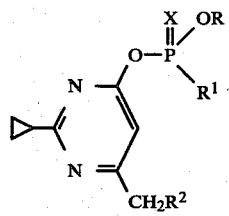

in which
R is alkyl with 1 to 5 carbon atoms,
$R^1$ is alkyl, alkoxy, alkylthio or alkylamino each with 1 to 5 carbon atoms, or phenyl,
$R^2$ is alkoxy or alkylthio with 1 to 5 carbon atoms, and
X is oxygen or sulphur.

2. A compound according to claim 1, wherein such compound is O,O-diethyl-O-(2-cyclopropyl-6-methoxymethyl-pyrimidin-4-yl)-thionophosphoric acid ester of the formula

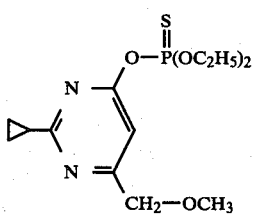

3. A compound according to claim 1, wherein such compound is O-ethyl-O-(2-cyclopropyl-6-methoxymethyl-pyrimidin-4-yl)-ethanethionophosphonic acid ester of the formula

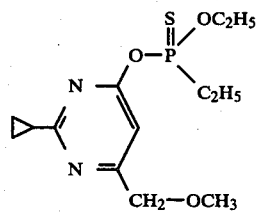

4. A compound according to claim 1, wherein such compound is O,O-diethyl-O-(2-cyclopropyl-6-methylthiomethyl-pyrimidin-4-yl)-thionophosphoric acid ester of the formula

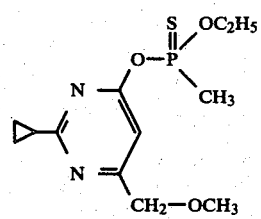

5. A compound according to claim 1, wherein such compound is O-isopropyl-O-(2-cyclopropyl-6-methoxymethyl-pyrimidin-4-yl)-methane-thionophosphonic acid ester of the formula 6. A compound according to claim 1, wherein such compound is O-ethyl-O-(2-cyclopropyl-6-methoxymethyl-pyrimidin-4-yl)-methanethionophosphonic acid ester of the formula 7. An arthropodicidal composition containing as active ingredient an arthropodicidally effective amount of a compound according to claim 1 in admixture with a diluent.

8. A method of combating arthropods which comprises applying to the arthropods, or to a habitat thereof, an arthropodicidally effective amount of a compound according to claim 1.

9. The method according to claim 8, in which said compound is
O,O-diethyl-O-(2-cyclopropyl-6-methoxymethyl-pyrimidin-4-yl)-thionophosphoric acid ester,
O-ethyl-O-(2-cyclopropyl-6-methoxymethyl-pyrimidin-4-yl)-ethanethionophosphonic acid ester,
O,O-diethyl-O-(2-cyclopropyl-6-methylthiomethyl-pyrimidin-4-yl)-thionophosphoric acid ester,
O-isopropyl-O-(2-cyclopropyl-6-methoxymethyl-pyrimidin-4-yl)-methane-thionophosphonic acid ester or
O-ethyl-O-(2-cyclopropyl-6-methoxymethyl-pyrimidin-4-yl)-methanethionophosphonic acid ester.